US006007807A

United States Patent [19]

Mocikat et al.

[11] Patent Number: 6,007,807

[45] Date of Patent: Dec. 28, 1999

[54] INDUCTION OF TUMOUR IMMUNITY BY INJECTION OF HYBRID CELLS

[75] Inventors: Ralf Mocikat, Munich; Horst Lindhofer, Grobenzell; Stefan Thierfelder, Eichenau, all of Germany

[73] Assignee: GSF Forschungszentrum fur Umwelt und Gesundheit GmbH, Oberschleissheim, Germany

[21] Appl. No.: 08/917,216

[22] Filed: Aug. 25, 1997

[30] Foreign Application Priority Data

Aug. 23, 1996 [DE] Germany .......................... 196 34 159

[51] Int. Cl.[6] ............................ A61K 35/00; C12N 15/85

[52] U.S. Cl. .................... 424/93.21; 424/93.2; 435/328; 435/334; 435/346

[58] Field of Search ............................... 424/93.2, 93.21; 435/327, 328, 346, 334

[56] References Cited

FOREIGN PATENT DOCUMENTS 44 19 399 C1 9/1995 Germany .

OTHER PUBLICATIONS

Mocikat et al. (1997) Cancer Research, vol. 57, 2346–2349, Jun. 1997.

Restifo et al. (1993) Journal of Immunology, vol. 14, 182–190, 1993.

Orkin et al. (1995) "Report and Recommendations of the Panetl to Assess the NIH Investment in Research on Gene Therapy" 1995.

Ross et al. (1996) Human Gene Therapy, vol. 7, 1781–1790, Sep. 1996.

Vieweg et al. (1995) Cancer Investigation, vol. 13(2), 193–201, 1995.

Enhanced Antigen Immunogenicity Induced by Bispecific Antibodies, Snider, Journal of Experimental Medicine, vol. 171, Jun. 1990 1957–1963.

Effective Tumor Vaccine Generated by Fusion of Hepatoma Cells with Activated B Cells, Guo, et al., Science, Vo. 263, Jan. 28, 1994.

Continuous Cultures of Fused Cells Secreting Antibody of Predefined Specificity, Nature Vo. 256, Aug. 7, 1975.

*Primary Examiner*—Deborah Crouch
*Assistant Examiner*—Anne Marie S. Beckerleg
*Attorney, Agent, or Firm*—Sixbey, Friedman, Leedom & Ferguson, P.C.; Robert M. Schulman

[57] ABSTRACT

A hybrid fusion cell comprising:

a) a malignant B cell which expresses an idiotypic antibody; and b) a hybridoma which expresses an antibody which is capable of being internalized on a professional antigen presenting cell.

15 Claims, 2 Drawing Sheets

INDUCTION OF TUMOUR IMMUNITY BY INJECTION OF HYBRID CELLS

BACKGROUND OF THE INVENTION (i) Field of the Invention

The present invention relates to a hybrid cell and to the use thereof for the induction of tumor immunity by injection into a patient suffering from B cell neoplasia.

(ii) Description of Related Art

Despite the progress in chemotherapy and radiotherapy made in the last years, malignant disorders of B cells in man (B cell neoplasias), such as B cell lymphomas, still have an extraordinarily unfavorable prognosis. It is impossible to cure these diseases. Therefore, it is neccessary to develop new treatment strategies. In this respect, great hopes are placed in immunotherapeutical approaches, which shall induce rejection of the tumor by the immune system of the patient.

It is known that tumor-associated antigens are present on tumor cells and that in principle the immune system is able to recognize these antigens and attack the malignant cells. Tumors have, however, developed certain strategies which enable them to escape the immune reaction. For example, this is possible by insufficient presentation of tumor associated antigens and/or insufficient activation of the tumor-specific T cells which are generally present.

Malignant B cells, such as B cell lymphomas, are unique because they bear an absolutely tumor-specific antigen, namely the idiotype of the immunoglobulin expressed by them. This, however, represents a very weak immunogen.

SUMMARY AND OBJECTS OF PREFERRED EMBODIMENTS

It is an object of the present invention to provide a new agent for the therapy of malignant diseases of the B cells in humans.

This object has been achieved according to the invention by the hybrid cell characterized in more detail in the claim. Preferred embodiments of the invention become evident by the dependent claims. The hybrid cell line provided by the invention is used to induce a tumor immunity by injection of the hybrid cell into a patient suffering from B cell neoplasia of whom the malignant B cell is derived.

The solution of this object according to the invention is aimed at the induction of an efficient T cell reaction against the idiotype by enhancing the presentation thereof on professional antigen-presenting cells (APCs) and thereby achieving an effective T cell activation.

DETAILED DESCRIPTION OF PERFERRED EMBODIMENTS

Figure 1:
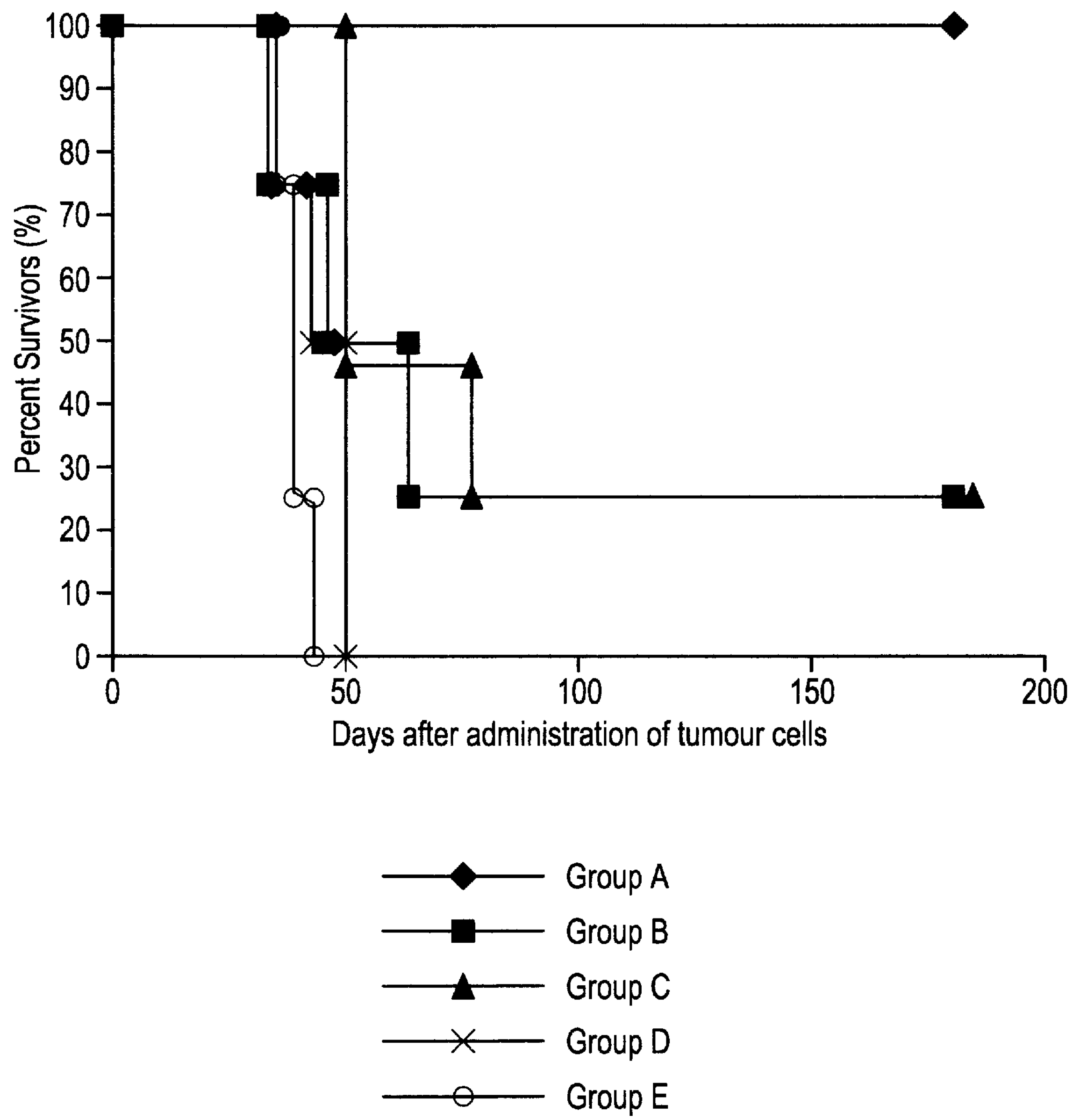
FIG. 1 is a graph depicting the percentage of cells surviving as a function of days after administration of tumor cells after injection of mice with BIV cells.

The invention is based on the specific redirection of the tumor idiotype against professional APCs. To achieve this, malignant B cells, such as lymphoma cells, from patients are fused to a hybridoma producing antibodies against proteins on the surfaces of APCs. The hybrid tumor cells are infused back to the patient. In this manner, it is possible to achieve the following:

The hybrid tumor cells secrete a bispecific antibody (bsAb) which on the one hand contains tumor-specific immunoglobulin (1 H and 1 L chain) and on the other hand an antibody semimolecule (1 H and 1 L chain) recognizing a surface antigen on APCs. Due to the binding to APCs, the tumor idiotype is internalized, processed, and presented to the immune system in the form of tumor-specific peptides. In contrast to the incomplete presentation on the tumor cell, tumor-specific T cells can be generated by the "professional" presentation of the tumor antigen on the APC. Due to the xenogenic portion of the hybrid cell which is derived from the fusion partner of the malignant B cell—the mouse or rat hybridoma—it is recognized as nonself and destroyed by the immune system in relatively short time.

This has two advantages, namely, that these artificial cells destroy themselves in the patient and, second, a further enhancement of the tumor immunity by phagocytosis of the lysed cells and subsequent presentation of additional tumor antigens is achieved. This leads to the production of a significantly improved anti-tumor effectivity by injection of the hybrid cells as compared to injection of the bsAb produced and purified ex vivo.

After fusion of two antibody-producing cells generally a mixed population of bivalent antibodies exhibiting different H/L chain pairings is obtained. An important prerequisite for the injection of the bsAb-producing cells into the host bearing the tumor is the found preferential H/L pairing between chains of the same specificity. This is observed when cells of different species origin are fused to each other (process for the preparation of heterologous bispecific antibodies, DE-A-44 19 399, Mar. 9, 1995). The hybrid tumor cells reinjected into the host express the desired bispecific construct in high yield.

But not only the xenogenic nature of the hybrid cell contributes to the mediation of the achieved anti-tumor effect, since a hybrid cell secreting a bsAb having a defective APC binding arm is not able to induce a complete tumor protection. Nevertheless, by its synergistic action with the mechanism of the specific idiotype redirection the xenogenic portion seems to be of importance. Because of the xenogenic properties of the hybrid cell it is no longer necessary to carry out irradiation prior to injection. This is an advantage as compared to previous procedures of cellular vaccination.

Prior to injection, it is also possible to render the hybrid cells replication incompetent by irradiation without interfering with the expression of the bsAb. A further advantage of injecting the patient with the bsAb-producing hybrid cells is that complicated steps of production and purification for the preparation of the bsAb in clinically relevant amounts become unnecessary. Eventually, it is of importance that the adaptives of the malignant B cells to the growth in cell culture which generally is problematic in the case of human tumors is no longer required. No cell division is required for the fusion of the cells to the hybridoma.

The malignant B cell which is fused to the hybridoma cell may for example be a B cell leukemia cell, a B cell lymphoma cell, or a plasmocytoma cell.

The hybridoma cell is derived from the fusion of a lymphocyte producing an antibody directed against a surface antigen on an APC to a myeloma cell. The surface antigen may for example be a Fc receptor, a mannose-5 receptor, or a MHC class II antigen. The hybridoma cell is prepared using procedures known per se. Examplarily, it is referred to in the first publication by Kohler and Milstein, Nature volume 256, 495–497 (1975) and to Rompp Lexikon Biotechnologie, Georg Thieme-Verlag, Stuttgart, New York, 1992, page 379. In particular, there may be used already existing and also commercially available hybridoma cells which shows the required characteristics. For example, reference is made in this respect to the anti-Fc receptor hybridoma cell line 2.4G2 available at the American Type Culture Collection (ATCC HB-197).

The hybrid cell provided according to the invention is administered to the patient in a therapeutically effective amount, preferably together with an acceptable carrier and/or excipients optionally after purification. The pharmaceutical composition provided according to the invention containing the hybrid cell of the invention in a therapeutically effective amount is administered to a patient suffering from B cell neoplasia for example by injection. B cell neoplasias include for example B cell leukemias, B cell lymphomas, and plasmocytomas.

The immunoglobulins produced by the malignant B cell assemble with the immunoglobulin of the antibody-producing hybridoma cell to form bispecific antibodies. These bispecific antibodies are preferably secreted into the surrounding medium. This bispecific antibody is able to bind to a surface antigen on an antigen-presenting cell and in particular to bind to Fc receptors, mannose-5 receptors, and to MHC class II antigens.

The following references are cited as prior art, which, however, neither describe nor make obvious the present invention.

Snider et al., J. Exp. Med. 1957–1963 (1990) describe that an antigen (in this case lysozyme from egg-white of hens) has a strong immunogenic activity even in low doses if it is directed against antigen-presenting cells. In the above publication, this is achieved by means of bispecific antibodies which bind to the antigen and with their other binding arm also recognize surface molecules on the APCs (Fc receptor or MHCII).

Guo et al. describe in Science 518–520, volume 263, 1994 a hepatoma model of the rat. The animals are vaccinated against the wild-type tumor by administration of hybrid tumor cells, but an immunization against a specific tumor antigen with a defined molecule is impossible. The hybrid cells do not produce a bispecific immunoglobulin directing the tumor antigen against professional APCs, but instead the hybrid tumor cell itself becomes the APC. This is achieved by fusion of the tumor cell to activated B cells.

In the following, the invention is described in more detail with respect to the practical example and two Figures.

EXAMPLE

1) The B cell lymphoma A20 derived from the BALB/c mouse (ATCC TIB-208) is fused to the anti-Fc receptor hybridoma 2.4G2 (ATCC HB-197). Both cell lines are commercially available at the American Type Culture Collection under the numbers indicated. For fusion, the hybridoma is HAT-sensitized in culture in the presence of 8-azaguanine. $5\times10_6$ cells of the fusion partner are incubated for 30 minutes in iodoacetamide, washed and mixed with $1.5\times10^7$ HAT-sensitized cells. The fusion is carried out by incubation for two minutes with polyethylenglycol 1500. The cells are seeded in microtiter plates and after two to three days are introduced in HAT-medium for selection.

2) BALB/c mice are twice injected i.p. with an interval of 3 weeks with $10_5$ hybrid cells (BiV cells) at each injection. 7 days later the inoculation i.p. with $10^5$ wild-type tumor cells (A20) is performed. By the preimmunisation a long-lasting tumor protection can be achieved (see FIG. 1). A further inoculum after more than 100 days is also rejected. An immunisation using $10^3$ hybrid cells is not as successful. Hybrid cells secreting an antibody which is unable to bind to APCs fail to show anti-tumor effectivity (BiVneg).

Figure 2:
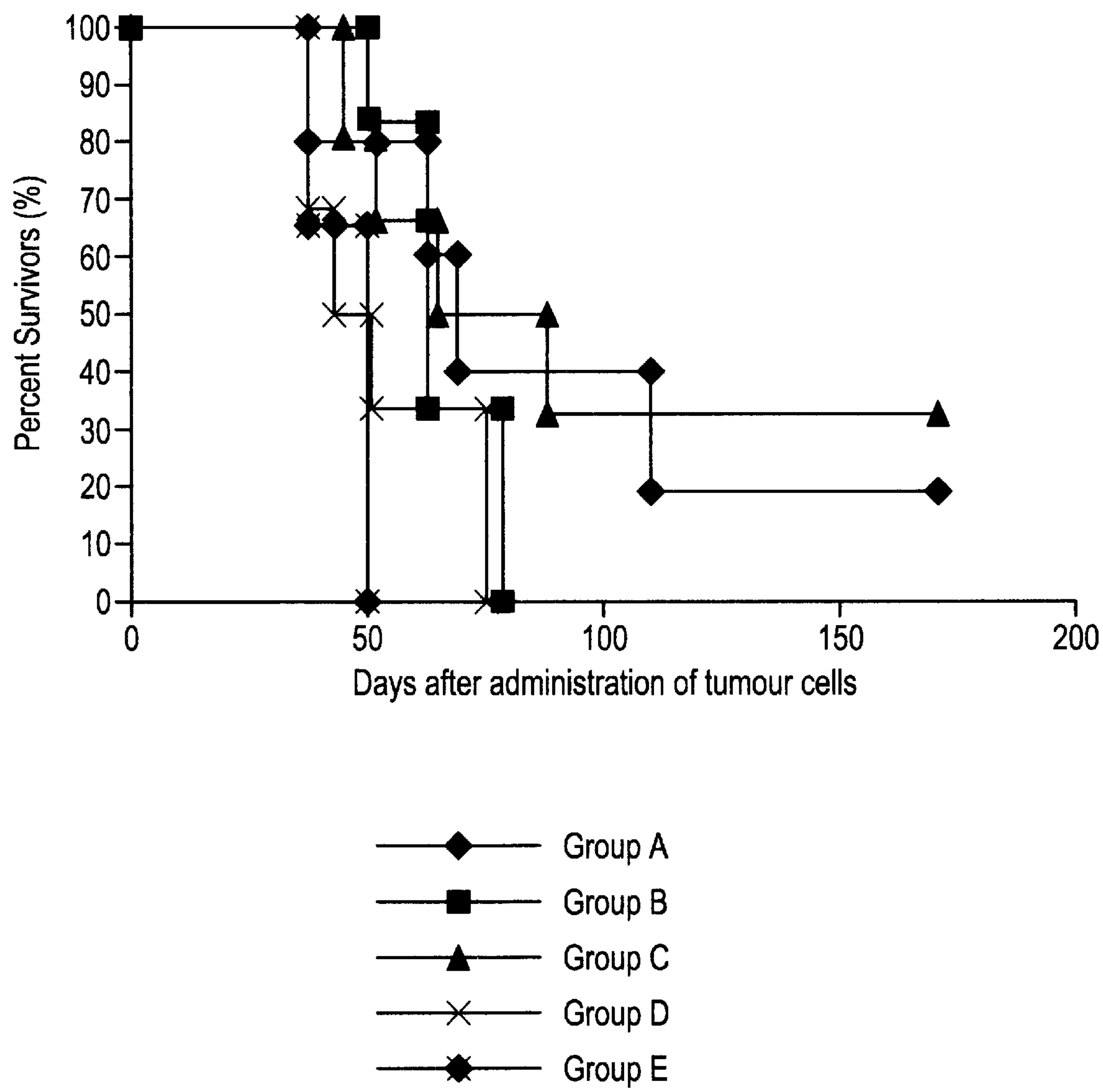
FIG. 2 is a graph depicting the percentage of cells surviving as a function of days after administration of tumor cells after injection of mice with BiV proteins.

3) The bispecific antibody secreted by the BiV cells is purified by chromatography on a protein-A-sepharose column. The bsAb is eluted from the column in 0.1 M citrate buffer pH 5.8 and dialysed against PBS. 50 $\mu$g of the purified bsAb (BiV protein), of the purified monospecific immunoglobulin of the A20 tumor, or a mixture of 25 $\mu$g each of this immunoglobulin and the anti-Fc receptor antibody, respectively, are injected i.p. into BALB/c mice. After a further immunization carried out 21 days later $10^5$ wild-type tumor cells are injected with an interval of 7 days (FIG. 2).

The invention has been described above with respect to an example carried out using an animal model. Longstanding experience shows that the results obtained in this way can be applied to humans as well. The invention has been described above by means of a specific practical example. It shall be understood that the invention is not restricted to this specific practical example, but that it can be varied in the scope of the following claims.

We claim:

1. A hybrid fusion cell comprising a fusion product of:

a) a malignant B cell which expresses an idiotypic antibody; and b) a B cell hybridoma which expresses an antibody which is capable of being internalized on a professional antigen presenting cell.

2. The hybrid cell according to claim 1, wherein said malignant B cell is a B cell leukemia cell, a B cell lymphoma cell, or a plasmocytoma cell.

3. The hybrid cell according to claim 1, wherein said hybridoma cell is a fusion of (i) a lymphocyte producing an antibody against a surface antigen on an APC to (ii) a myeloma cell.

4. The hybrid cell according to claim 1, wherein said malignant B cell produces immunoglobulins which assemble with the immunoglobulin of the antibody-producing hybridoma cell to form bispecific antibodies.

5. The hybrid cell according to claim 4, which is present in a surrounding medium and wherein said bispecific antibody is secreted into the surrounding medium.

6. Hybrid cell according to claim 4, wherein said bispecific antibody binds to Fc receptors.

7. The hybrid cell according to claim 4, wherein said bispecific antibody binds to MHC class II antigens.

8. Hybrid cell according to claim 1, wherein said hybrid cell is not replication incompetent.

9. Hybrid cell according to claim 1, wherein said hybrid cell is replication incompetent.

10. Hybrid cell according to claim 1, wherein said surface antigen on the antigen-presenting cell is a Fc receptor, or a MHC class II antigen.

11. A pharmaceutical composition comprising:

(i) the hybrid fusion cell according to claim 1, in a therapeutically effective amount; and (ii) at least one of one or more pharmaceutically acceptable carriers and excipients.

12. A process for the preparation of a hybrid fusion cell according to claim 1, comprising the step of fusing a malignant B cell derived from a patient to a B cell hybridoma cell producing an antibody which binds to a surface antigen on an antigen-presenting cell (APC).

13. A method for treating a patient suffering from B cell neoplasia comprising injecting into said patient the hybrid fusion cell according to claim 1, wherein said hybrid cell is made from a malignant B cell obtained from the patient being treated, and wherein said hybrid fusion cell generates a tumor specific immune response in said patient.

14. The method according to claim 13, further comprising the step of rendering said hybrid fusion cell replicationincompetent prior to the step of injecting said fusion cell into the patient.

15. The method according to claim 13, wherein said hybrid cell is rendered replication incompetent by irradiation.

* * * * *